United States Patent
Ujibashi et al.

(10) Patent No.: US 10,861,585 B2
(45) Date of Patent: Dec. 8, 2020

(54) INFORMATION PROCESSING APPARATUS AND METHOD OF COLLECTING GENOME DATA

(71) Applicant: FUJITSU LIMITED, Kawasaki (JP)

(72) Inventors: Yoshifumi Ujibashi, Kawasaki (JP); Minoru Nakamura, Kawasaki (JP)

(73) Assignee: FUJITSU LIMITED, Kawasaki (JP)

( * ) Notice: Subject to any disclaimer, the term of this patent is extended or adjusted under 35 U.S.C. 154(b) by 614 days.

(21) Appl. No.: 15/700,802

(22) Filed: Sep. 11, 2017

(65) Prior Publication Data

US 2018/0082013 A1 Mar. 22, 2018

(30) Foreign Application Priority Data

Sep. 16, 2016 (JP) .................................. 2016-181677

(51) Int. Cl.
*G01N 33/48* (2006.01)
*G06F 15/00* (2006.01)
*G16B 20/00* (2019.01)
*G16B 30/00* (2019.01)

(52) U.S. Cl.
CPC ............. *G16B 20/00* (2019.02); *G16B 30/00* (2019.02)

(58) Field of Classification Search
None
See application file for complete search history.

(56) References Cited

U.S. PATENT DOCUMENTS

| | | | | |
|---|---|---|---|---|
| 7,917,302 B2* | 3/2011 | Rognes | ................. | G16B 30/00 702/20 |
| 9,165,253 B2* | 10/2015 | Cleary | ................. | G06N 5/048 |
| 2001/0028741 A1 | 10/2001 | Fahraeus et al. | | |
| 2008/0086274 A1* | 4/2008 | Chamberlain | ......... | G16B 30/00 702/19 |

FOREIGN PATENT DOCUMENTS

JP 2002-509316 3/2002

OTHER PUBLICATIONS

Zhou, Jingren, and Kenneth A. Ross. "Implementing database operations using SIMD instructions." Proceedings of the 2002 ACM SIGMOD international conference on Management of data. 2002.*
World Intellectual Property Organization English abstract for International Publication No. WO 99/36879 published Jul. 22, 1999 corresponding to Japanese Publication No. 2002-509316.

* cited by examiner

*Primary Examiner* — Anna Skibinsky
(74) *Attorney, Agent, or Firm* — Staas & Halsey LLP

(57) ABSTRACT

An information processing apparatus includes a memory and a processor coupled to the memory and configured to extract data having x times y bits from genome data in which a mutation pattern at each gene mutation position is represented as x bits, such that the extracted data is constituted by y data pieces each having x bits at y respective mutation positions, x and y being integers greater than or equal to 1, respectively, to refer to an addend table that stores a plurality of addend data associated with respective x-times-y-bit data to identify addend data corresponding to the extracted data, and to use an SIMD instruction to add the identified addend data to count data at positions corresponding to the y mutation positions in the genome data, the count data indicating counts of occurrences of mutation patterns in the genome data.

5 Claims, 10 Drawing Sheets

INFORMATION PROCESSING APPARATUS AND METHOD OF COLLECTING GENOME DATA

CROSS-REFERENCE TO RELATED APPLICATIONS

The present application is based upon and claims the benefit of priority from the prior Japanese Patent Application No. 2016-181677 filed on Sep. 16, 2016, with the Japanese Patent Office, the entire contents of which are incorporated herein by reference.

FIELD

The disclosures herein relate to an information processing apparatus, a program for collecting genome data, and a method of collecting genome data.

BACKGROUND

In recent years, attempts have been made to analyze the DNA sequence of humans or the like to identify diseases-related genes. For example, the numbers of occurrences of mutation patterns at the positions of mutation occurring in genes are collected based on big data of the DNA sequence of humans or the like. A difference in the mutation-pattern distribution is analyzed by comparing a group of people having a specific disease with a group of people having no such disease, thereby identifying the disease-related genes.

The DNA sequence of a single human includes tens of millions of positions at which gene mutation patterns may occur. Collecting the numbers of occurrences of gene mutation patterns is thus time consuming.

RELATED-ART DOCUMENTS

Patent Document

[Patent Document 1] Japanese National Publication of International Patent Application No. 2002-509316

SUMMARY

According to an aspect of the embodiment, an information processing apparatus includes a memory and a processor coupled to the memory and configured to extract data having x times y bits from genome data in which a mutation pattern at each gene mutation position is represented as x bits, such that the extracted data is constituted by y data pieces each having x bits at y respective mutation positions, x and y being integers greater than or equal to 1, respectively, to refer to an addend table that stores a plurality of addend data associated with respective x-times-y-bit data to identify addend data corresponding to the extracted data, and to use an SIMD instruction to add the identified addend data to count data at positions corresponding to the y mutation positions in the genome data, the count data indicating counts of occurrences of mutation patterns in the genome data.

The object and advantages of the embodiment will be realized and attained by means of the elements and combinations particularly pointed out in the claims. It is to be understood that both the foregoing general description and the following detailed description are exemplary and explanatory and are not restrictive of the invention, as claimed.

DESCRIPTION OF EMBODIMENTS

In the following, embodiments of the present invention will be described with reference to the accompanying drawings.

Figure 1:
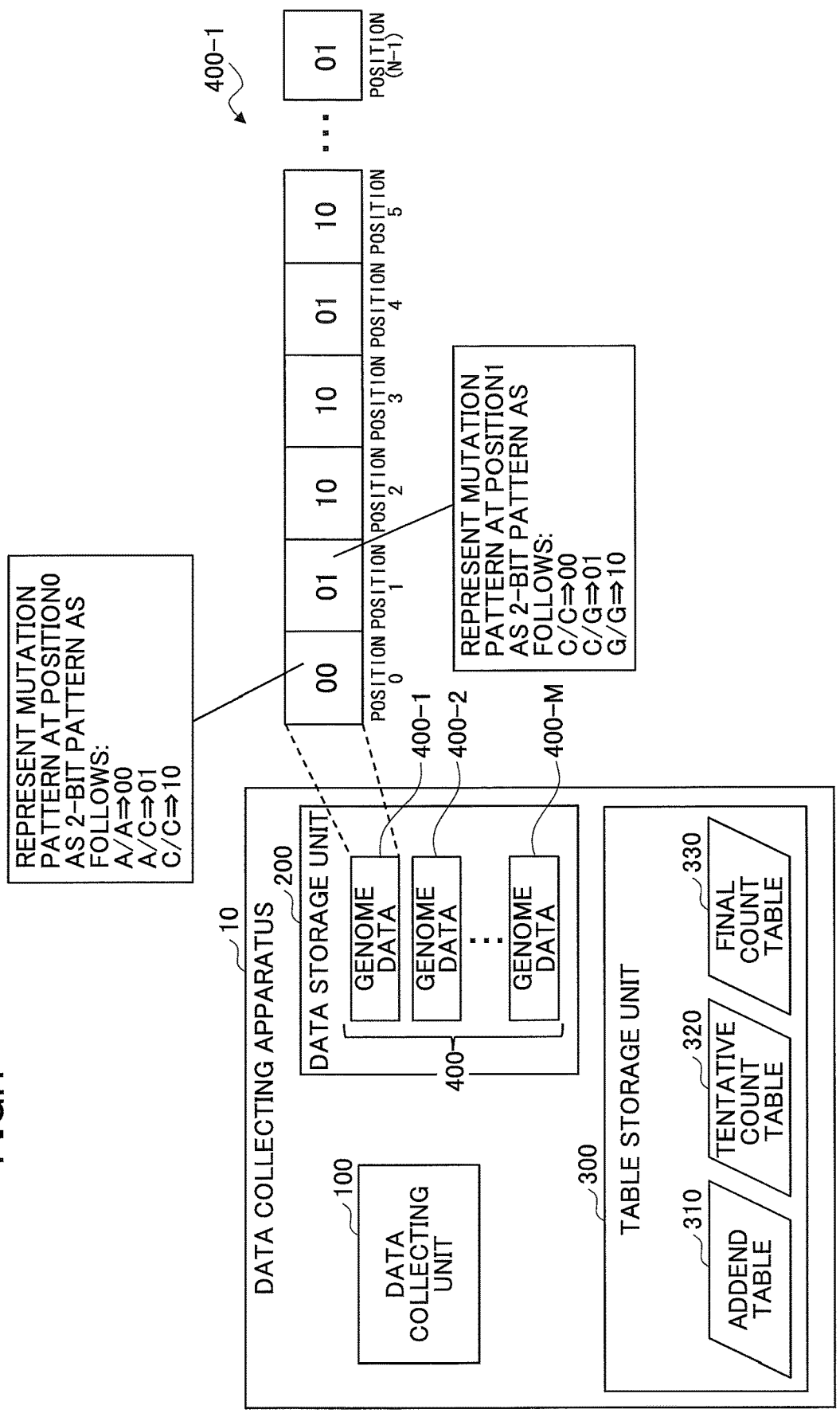
FIG. 1 is a drawing illustrating an example of the entire configuration of a data collecting apparatus according to an embodiment.

A data collecting apparatus 10 of the present embodiment will be described by referring to FIG. 1. FIG. 1 is a drawing illustrating an example of the entire configuration of the data collecting apparatus 10 according to the present embodiment.

The data collecting apparatus 10 illustrated in FIG. 1, which is an information processing apparatus such as a personal computer, includes a data collecting unit 100, a data storage unit 200, and a table storage unit 300.

The data storage unit 200 stores genome data 400 for a plurality of people. Namely, the data storage unit 200 stores genome data 400-1 for a first person, genome data 400-2 for a second person, . . . , and genome data 400-M for an M-th person. In the following, the term "genome data 400" is used when the genome data 400-1, the genome data 400-2, . . . , and the genome data 400-M are not discriminated from each other.

The genome data 400 used in the present embodiment represents mutation patterns as a bit sequence having two bits with respect to each position at which an SNP (single nucleotide polymorphism) occurs in the DNA sequence of humans or the like.

As illustrated in FIG. 1, the SNP patterns at a specific position (which is herein referred to as "POSITION0") in the DNA sequence of humans or the like may be "A/A", "A/C", and "C/C". In this case, the mutation patterns at the "POSITION0" in the genome data 400 may be represented as "00", "01", and "10", which are a bit sequence constituted by two bits.

Similarly, the SNP patterns at another specific position (which is herein referred to as "POSITION1") in the DNA sequence of humans or the like may be "C/C", "C/G", and "G/G" as illustrated in FIG. 1. In this case, similarly, the mutation patterns at the "POSITION1" in the genome data 400 may be represented as "00", "01", and "10", which are a bit sequence constituted by two bits.

The genome data 400 represents mutation patterns as a bit sequence having two bits at each of the N positions at which SNPs occur in the DNA sequence of humans or the like. In other words, the genome data 400 is a series of arranged bit sequences each having two bits for representing mutation patterns at the position of an SNP.

It may be noted that the genome data 400 is not limited to such a configuration. The genome data 400 may alternatively represent the number of copies of CNVs (i.e., copy number variations) as a bit sequence having a predetermined number of bits with respect to each range within which CNVs occur, for example. The genome data 400 may alternatively represent the number of repeats such as VNTRs (i.e., variable number of tandem repeats) or STRPs (i.e., short tandem repeat polymorphisms) as a bit sequence having a predetermined number of bits with respect to each range within which such repeats occur.

The data collecting unit 100 performs a data collection process for the genome data 400 stored in the data storage unit 200. Namely, the data collecting unit 100 counts the number of occurrences of mutation patterns at each position with respect to the genome data 400 stored in the data storage unit 200.

The table storage unit 300 stores various types of tables for use by the data collecting unit 100 in collecting the genome data 400. The table storage unit 300 stores an addend table 310, a tentative count table 320, and a final count table 330.

The addend table 310 is a look-up table in which addend data to be added to the counts of occurrences of mutation patterns are stored. The tentative count table 320 stores tentative count data indicative of tentative counts with respect to the numbers of occurrences of mutation patterns. The final count table 330 stores final count data indicative of final counts with respect to the numbers of occurrences of mutation patterns.

Figure 2:
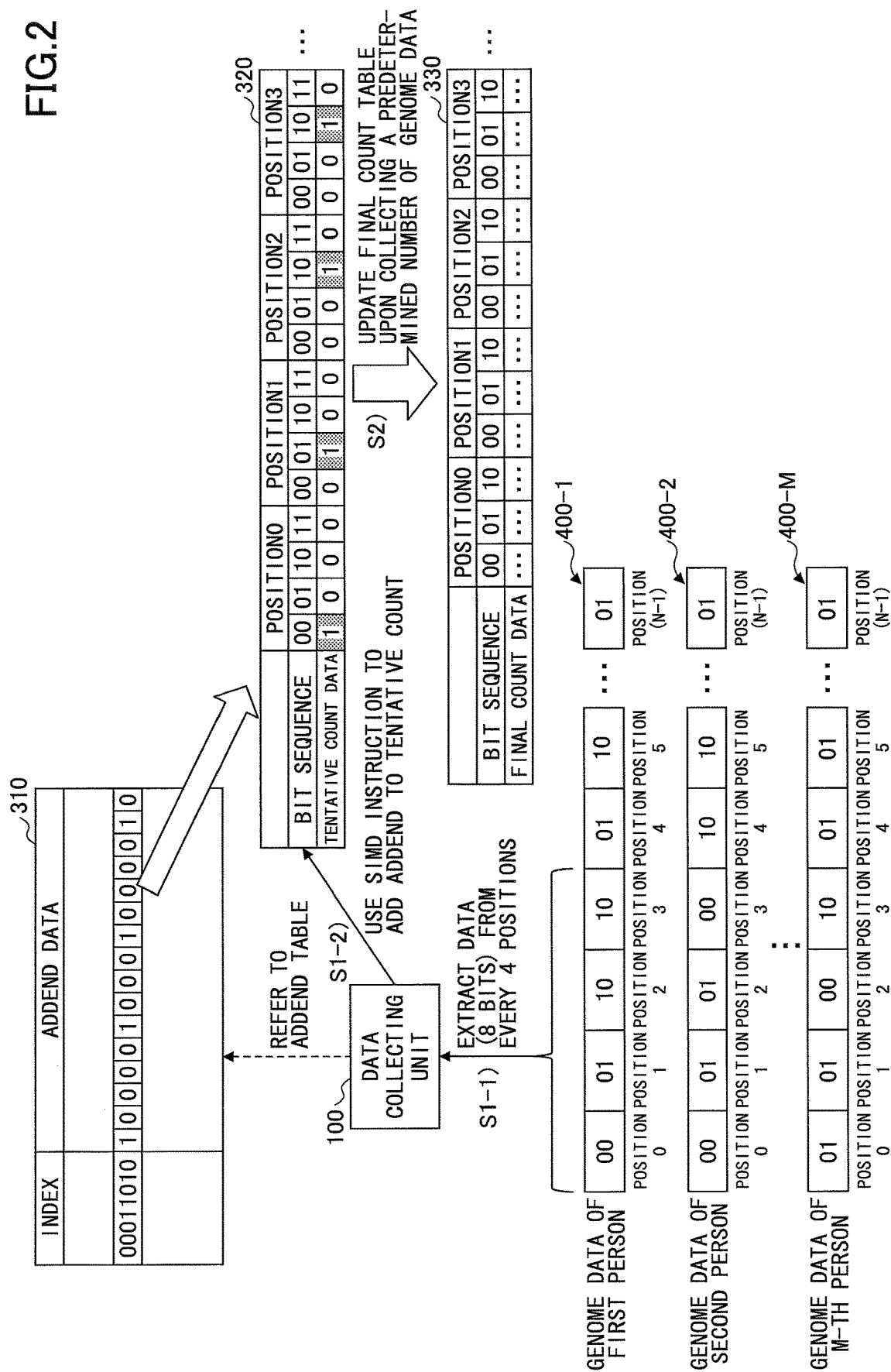
FIG. 2 is a drawing illustrating the outline of the data collection process according to the embodiment.

In the following, a description will be given of the outline of the data collection process performed by the data collecting apparatus 10 according to the present embodiment. FIG. 2 is a drawing illustrating the outline of the data collection process according to the present embodiment.

At step S1-1, the data collecting unit 100 extracts a bet sequence having 8 bits from POSITION0 to POSITION3 of the genome data 400-1. Namely, the data collecting unit 100 extracts the bit sequence "00011010" from POSITION0 through POSITION3.

At step S1-2, the data collecting unit 100 refers to the addend table 310 to identify the addend data corresponding to the same index as the extracted bit sequence, and uses an SIMD (single instruction multiple data) instruction to add the identified data to the tentative count data in the tentative count table 320.

Namely, the data collecting unit 100 uses an SIMD instruction to add the addend data "1000010001000010" corresponding to the index "00011010" in the addend table 310 to the tentative count data at POSITION0 through POSITION3 in the tentative count table 320. The data size of each digit of "1000010001000010" is 16 bits. The data size of the addend data is thus equal to 16 bits times 16, which is 256 bits. Through the above-noted addition operation, "1" is added to the tentative count data corresponding to the bit sequence "00" at POSITION0 in the tentative count table 320. Similarly, "1" is added to the tentative count data corresponding to the bit sequence "01" at POSITION1 in the tentative count table 320, to the tentative count data corresponding to the bit sequence "10" at POSITION2, and to the tentative count data corresponding to the bit sequence "10" at POSITION3.

The data collecting unit 100 further performs the processes of steps S1-1 and S1-2 noted above with respect to POSITION4 through POSITION7, POSITION8 through POSITION11, . . . , and POSITION(N−4) through POSITION(N−1) (i.e., the N−4-th position through the N−1-th position) of the genome data 400-1. Similarly, the data collecting unit 100 performs the processes of steps S1-1 and S1-2 noted above with respect to POSITION0 through POSITION3, . . . , and POSITION(N−4) through POSITION(N−1) of each of the genome data 400-2 through the genome data 400-M.

It may be noted that the number "N" of positions included in the genome data 400 is an integer multiple of 4. In the case of the number of positions in the genome data being not an integer multiple of 4, as many positions having the bit sequence "00" as appropriate may be added to the genome data 400, thereby making the number of positions in the genome data 400 equal to an integer multiple of 4.

At step S2, the data collecting unit 100 updates the final count table 330 based on the tentative count table 320 after a predetermined number of genome data 400 are tallied in the tentative count table 320. Namely, the data collecting unit 100 adds the tentative count data in the tentative count table 320 to the final count data in the final count table 330.

In this manner, the data collecting apparatus 10 of the present embodiment counts the numbers of occurrences of mutation patterns at each position with respect to a plurality of genome data 400. In so doing, as described in connection with the process of step S1-2, the data collecting apparatus 10 of the present embodiment refers to the addend table 310 to identify the addend data corresponding to the index, and, then, utilizes an SIMD instruction to add the identified addend data to the tentative count data in the tentative count table 320.

If an SIMD instruction was not used to count the numbers of occurrences of mutation patterns at POSITION0, for example, there would be a need to perform a 6-bit right circular shift with respect to the bit sequence at POSITION0 through POSITION3, followed by adding "1" to the tentative count data corresponding to the bit sequence obtained by masking the 6 most significant bits. Similarly, if an SIMD instruction was not used to count the numbers of occurrences of mutation patterns at POSITION1, for example, there would be a need to perform a 4-bit right circular shift with respect to the bit sequence at POSITION0 through POSITION3, followed by adding "1" to the tentative count data corresponding to the bit sequence obtained by masking the 6 most significant bits.

In this manner, counting the numbers of occurrences of mutation patterns at each position without utilizing a SIMD instruction involves the use of two instructions, i.e., one for a shift operation and the other for a masking operation. In contrast, the data collecting apparatus 10 of the present embodiment utilizes a single instruction (i.e., SIMD instruction) with respect to every four positions to count the numbers of occurrences of mutation patterns at these four positions as described above.

The data collecting apparatus 10 of the present embodiment is thus able to perform addition with respect to tentative count data without performing either a shift operation or a masking operation, thereby enabling high-speed counting of occurrences of mutation patterns.

As was in the above-noted example, the data collecting apparatus 10 of the present embodiment will be described as extracting one bit sequence from every four positions in the genome data 400, such that the mutation pattern at each of these positions is represented by two corresponding bits in the bits sequence. This is, however, not a limiting example. The data collecting apparatus 10 of the present embodiment may extract one bit sequence from every y positions in the genome data 400, such that the mutation pattern at each of these positions is represented by x corresponding bits in the bit sequence where x is an integer greater than or equal to 1, and y is an integer greater than or equal to 1.

In the case of y being an integer greater than or equal to 2, the data collecting apparatus 10 of the present embodiment is able to perform addition simultaneously at a plurality of positions with respect to the numbers of occurrences of mutation patterns. This arrangement thus enables faster counting of occurrences of mutation patterns. Because of this, y is preferably an integer that is two or greater.

Figure 3:
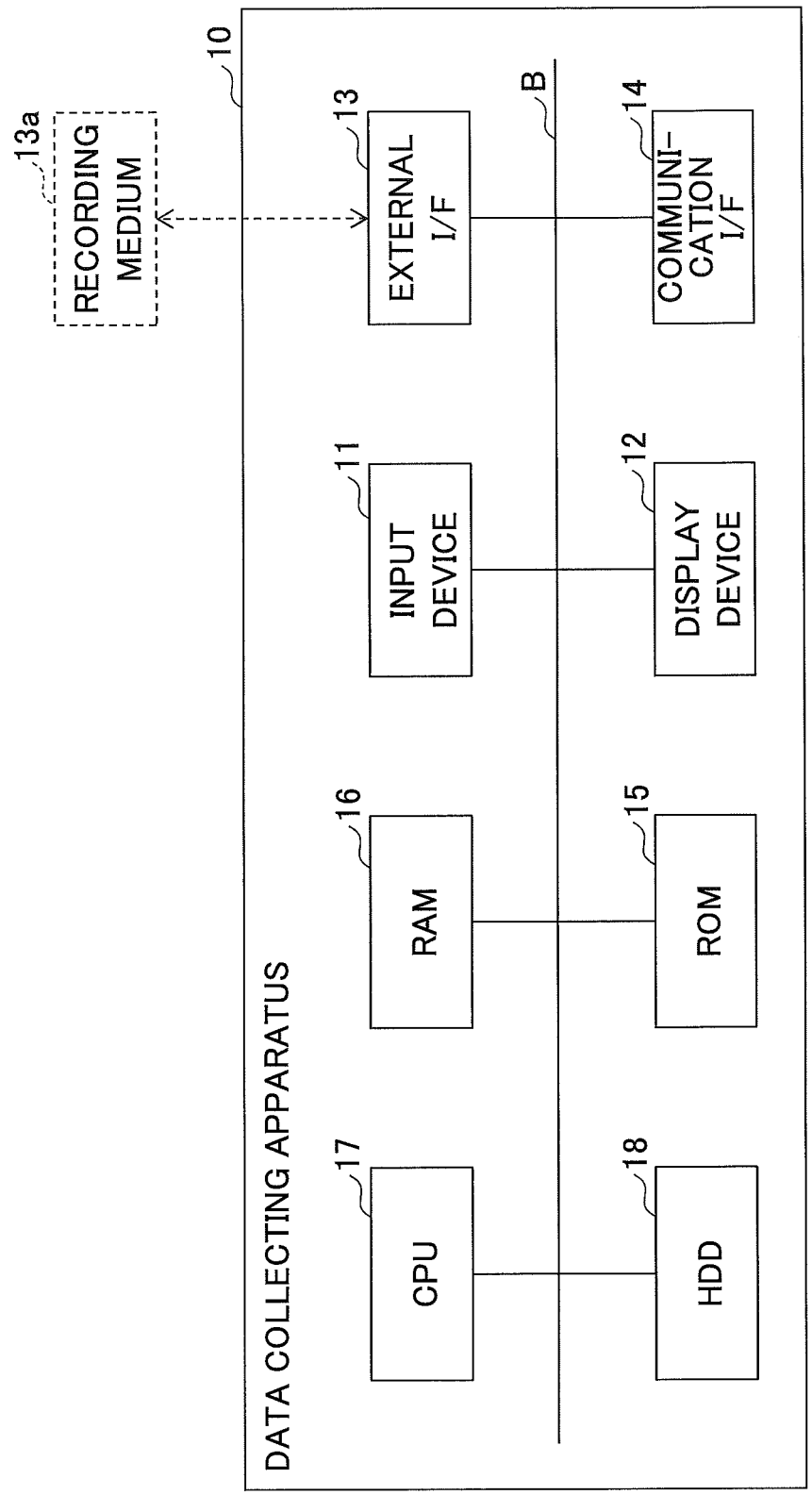
FIG. 3 is a drawing illustrating an example of the hardware configuration of the data collecting apparatus according to the embodiment.

In the following, a description will be given of the hardware configuration of the data collecting apparatus 10 according to the present embodiment by referring to FIG. 3. FIG. 3 is a drawing illustrating an example of the hardware configuration of the data collecting apparatus 10 according to the present embodiment.

As illustrated in FIG. 3, the data collecting apparatus 10 of the present embodiment includes an input device 11, a display device 12, an external I/F 13, and a communication I/F 14. The data collecting apparatus 10 of the present embodiment further includes a ROM (read only memory) 15, a RAM (random access memory) 16, a CPU (central processing unit) 17, and an HDD (hard disk drive) 18. These hardware units are coupled to each other through a bus B.

The input device 11 includes a keyboard, a mouse, a touch panel, and the like for use by a user in performing various operations. The display device 12 displays process results obtained by the data collecting apparatus 10. At least one of the input device 11 and the display device 12 may be configured to be coupled to the bus B only when such a need arises.

The communication I/F 14 is an interface for connecting the data collecting apparatus 10 to a network. The data collecting apparatus 10 performs data communication through the communication I/F 14.

The HDD 18 is a nonvolatile storage device that stores programs and data. The HDD 18 stores an OS (operating system) that is basic software for controlling the entirety of the data collecting apparatus 10, and also stores application software for providing various functions on the OS. The HDD 18 stores programs for implementing the data collecting unit 100 and the genome data 400.

The HDD 18 uses a file system or database to manage the programs and data stored therein.

The data collecting apparatus 10 may include a drive device utilizing flash memories as a memory medium (e.g., solid-state drive SSD).

The external I/F 13 is an interface for external apparatus. The external apparatus may include a recording medium 13a. The data collecting apparatus 10 performs read and write operations with respect to the recording medium 13a through the external I/F 13. The recording medium 13a may be a CD, a DVD, an SD-memory card, a USB memory stick, or the like.

The ROM 15 is a nonvolatile semiconductor memory (storage device) that can retain programs and data even when the power is switched off. The ROM 15 stores programs and data for OS settings, network settings, and the like as well as BIOS (basic input/output system) and the like that are executed at the time of activation of the data collecting apparatus 10. The RAM 16 is a volatile semiconductor memory that temporarily stores programs and data.

The CPU 17 loads programs and data into the RAM 16 from the memory devices such as the ROM 15 and the HDD 18, and performs processes based on these programs and data, thereby implementing the overall control and other functions of the data collecting apparatus 10. The CPU 17 of the data collecting apparatus 10 of the present embodiment is capable of processing 256-bit data in response to a SIMD instruction.

The data collecting apparatus 10 of the present embodiment has the hardware configuration illustrated in FIG. 3 to implement various processes as will be described later.

Figure 4:
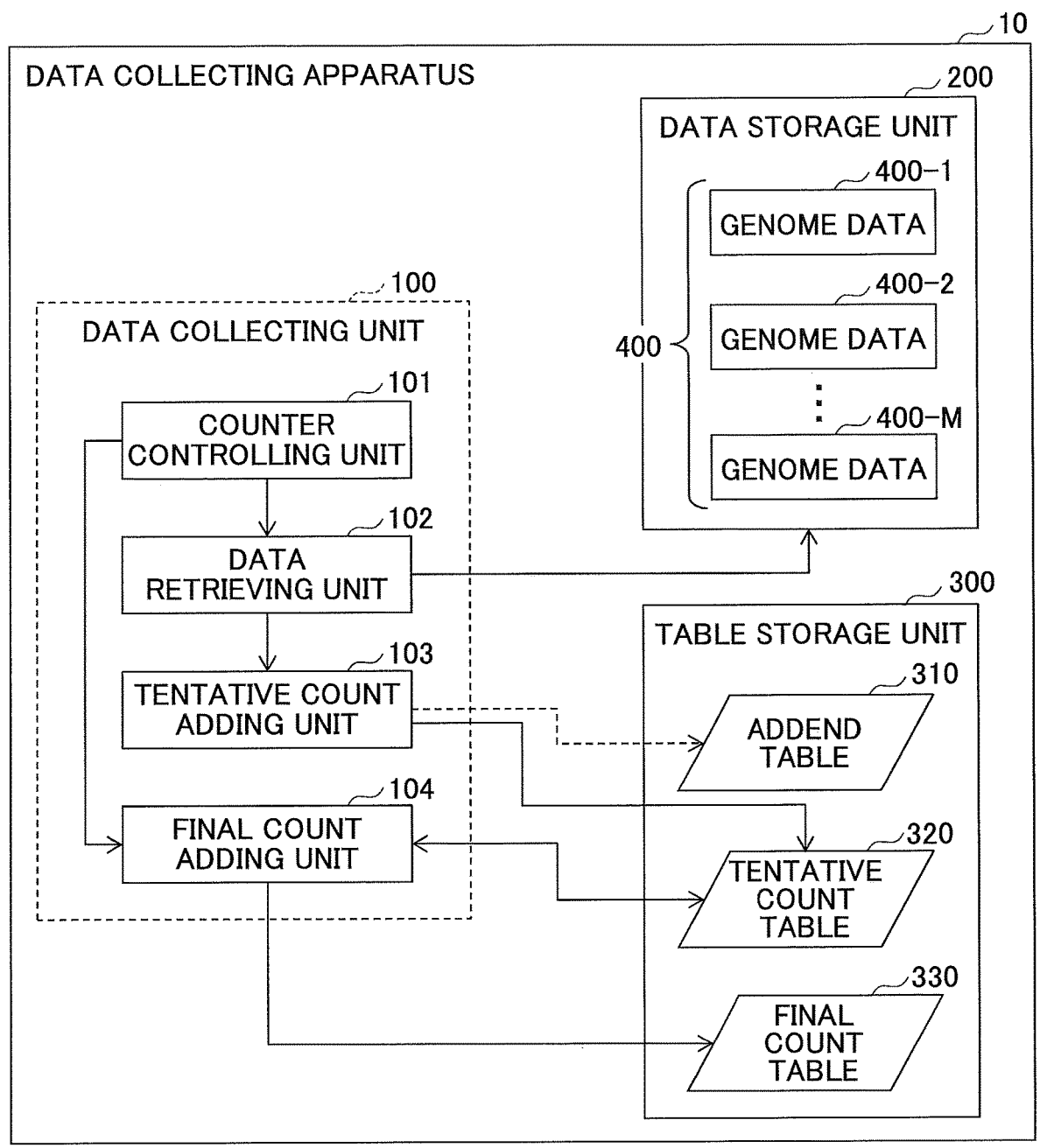
FIG. 4 is a drawing illustrating an example of the functional configuration of a data collecting unit of the data collecting apparatus according to the embodiment.

In the following, a description will be given of the functional configuration of the data collecting unit 100 of the data collecting apparatus 10 according to the present embodiment by referring to FIG. 4. FIG. 4 is a drawing illustrating an example of the functional configuration of the data collecting unit 100 of the data collecting apparatus 10 according to the present embodiment.

As illustrated in FIG. 4, the data collecting unit 100 of the present embodiment includes a counter controlling unit 101, a data retrieving unit 102, a tentative count adding unit 103, and a final count adding unit 104. The data collecting unit 100 is implemented as one or more processes that are performed by the CPU 17 under the control of one or more programs installed in the data collecting apparatus 10.

The counter controlling unit 101 controls various types of counters used in the data collection process. For example, the counter controlling unit 101 controls a counter m for indicating an m-th genome data 400-*m* stored in the data storage unit 200. Further, the counter controlling unit 101 controls a counter n for identifying POSITION(N) in the genome data 400.

The counter controlling unit 101 checks which one of the count of a given counter and a predetermined threshold is greater than the other. For example, the counter controlling unit 101 checks whether the count of the counter m is smaller than M+1. Further, the counter controlling unit 101 checks whether the count of the counter n is smaller than N.

The data retrieving unit 102 retrieves the genome data 400-*m* indicated by the counter m among the genome data 400 stored in the data storage unit 200.

The tentative count adding unit 103 extracts a bit sequence of POSITION(n) through POSITION(n+3) indicated by the counter n from the genome data 400-*m* retrieved by the data retrieving unit 102. The tentative count adding unit 103 refers to the addend table 310 to identify the addend data having the same index as the extracted bit sequence, and uses an SIMD instruction to add the identified addend data to the tentative count data of POSITION(n) through POSITION(n+3) in the tentative count table 320.

Figure 5:
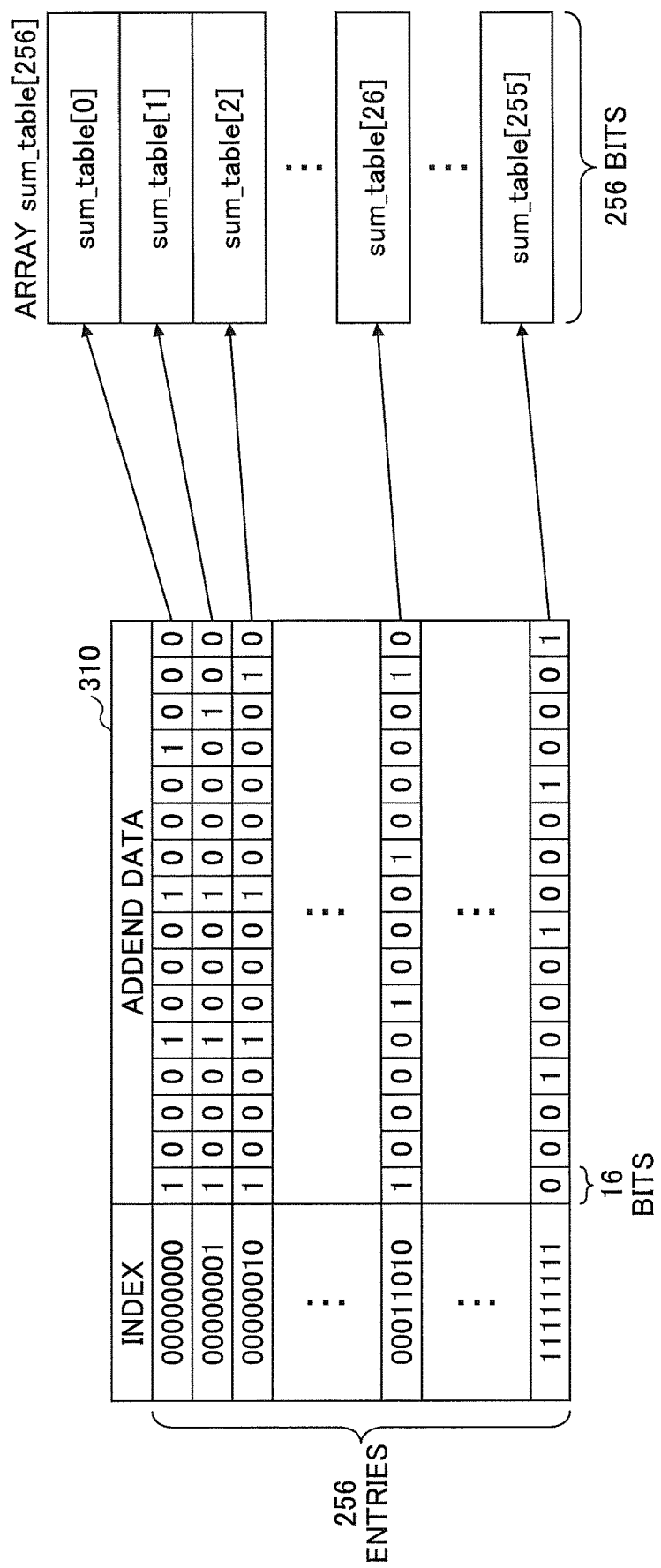
FIG. 5 is a drawing illustrating an example of an addend table.

The addend table 310 stored in the table storage unit 300 will be described by referring to FIG. 5. FIG. 5 is a drawing illustrating an example of the addend table 310.

As illustrated in FIG. 5, the addend table 310 of the present embodiment stores addend data associated with respective indexes each being an 8-bit sequence, for use in adding up the numbers of occurrences of mutation patterns.

The addend table 310 of the present embodiment has the indexes ranging from "00000000" to "11111111", which indicate that there are 256 entries of addend data. Each of the addend data stored in the addend table 310 of the present embodiment includes 16 addends, each of which has 16 bits.

The addend table 310 of the present embodiment may thus be implemented as sum table[256] which is an array of elements each having 256 bits. The array indexes "0"

through "255" for indicating the respective elements are expressed in 8 bits as the indexes of the addend table 310.

Each addend contained in given addend data has a value assigned thereto in correspondence with the index of the given addend data.

The index may be expressed as "$A_{00}A_{01}A_{10}A_{11}A_{20}A_{21}A_{30}A_{31}$". The addend may be expressed as "$X_{00}X_{01}X_{02}X_{03}X_{10}X_{11}X_{12}X_{13}X_{20}X_{21}X_{22}X_{23}X_{30}X_{31}X_{32}X_{33}$". Here, each $A_{ij}$ (i=0, 1, 2, 3; j=0, 1) is 1-bit long, and each $X_{kl}$ (k=0, 1, 2, 3; l=0, 1, 2, 3) is 16-bit long.

When "$A_{i0}A_{i1}$"="00" for a give value of i, "$X_{i0}X_{i1}X_{i2}X_{i3}$" is set to "1000".
When "$A_{i0}A_{i1}$"="01" for a give value of i, "$X_{i1}X_{i1}X_{i2}X_{i3}$" is set to "0100". When "$A_{i0}A_{i1}$"="10" for a give value of i, "$X_{i0}X_{i1}X_{i2}X_{i3}$" is set to "0010". When "$A_{i0}A_{i1}$"="11" for a give value of i, "$X_{i0}X_{i1}X_{i2}X_{i3}$" is set to "0001".

With the setting of each addend contained in each addend data as described above, an SIMD instruction is able to perform addition with respect to the tentative count data stored in the tentative count table 320.

Figure 6:
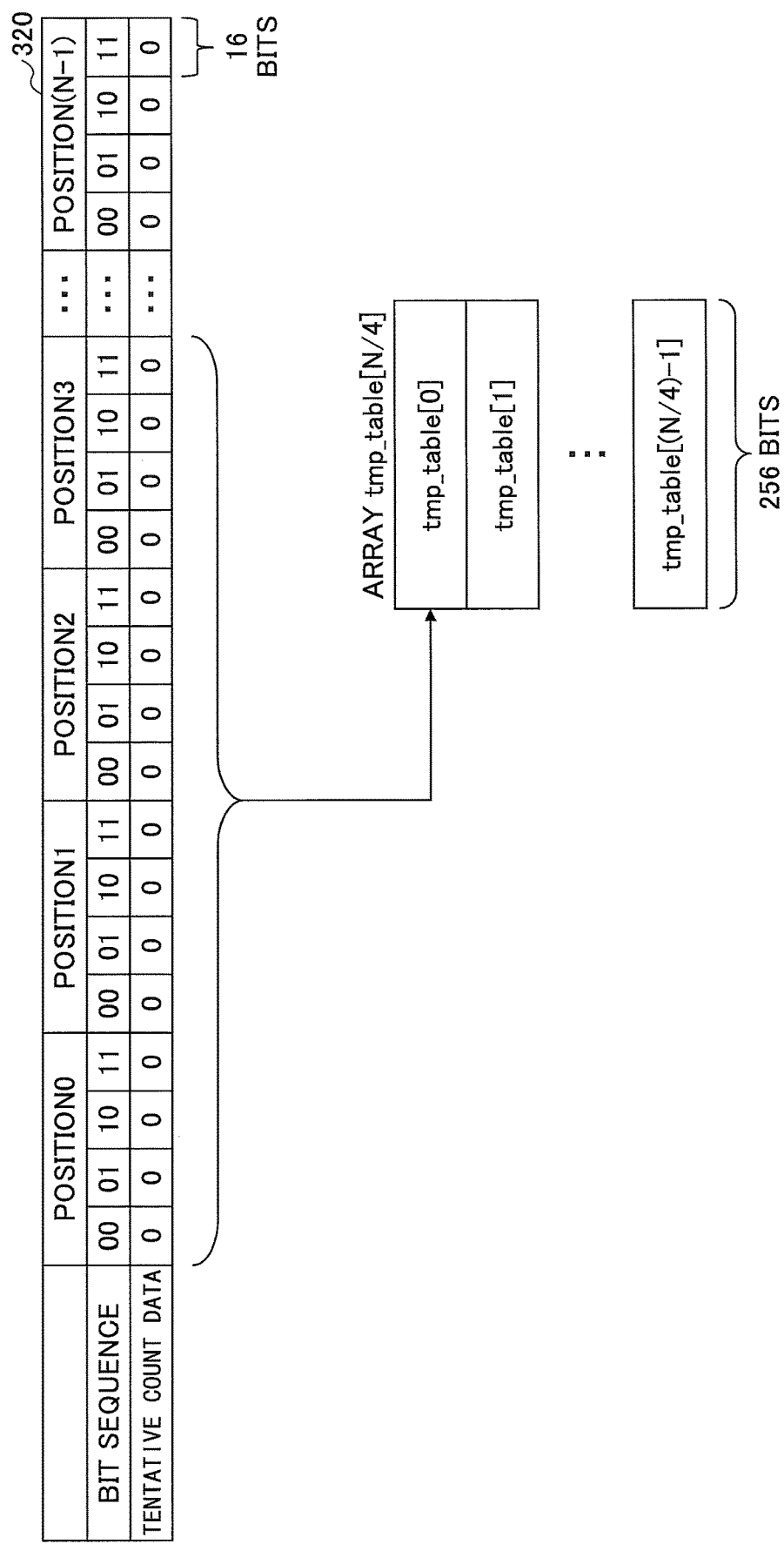
FIG. 6 is a drawing illustrating an example of a tentative count table.

The tentative count table 320 stored in the table storage unit 300 will be described by referring to FIG. 6. FIG. 6 is a drawing illustrating an example of the tentative count table 320.

As illustrated in FIG. 6, the tentative count table 320 of the present embodiment stores tentative count data indicative of the tentative counts of occurrences of mutation patterns such that the tentative count data are associated with positions in the genome data 400 and with bit sequences representing mutation patterns.

In the tentative count table 320 of the present embodiment, each tentative count data is represented as 16 bits. The tentative count table 320 of the present embodiment may thus be implemented as tmp_table[N/4] which is an array of elements each having 256 bits.

In this case, the array element "tmp_table[0]" stores the tentative count data of POSITION0 through POSITION3. The array element "tmp_table[1]" stores the tentative count data of POSITION4 through POSITION7. Similarly, the array element "tmp_table[(N/4)−1]" stores the tentative count data of POSITION(N−4) through POSITION(N−1).

As was previously described, each addend data in the addend table 310 includes 16 addends each of which is represented as 16 bits. Further, each of the 16 tentative count data at POSITION(n) through POSITION(n+3) in the tentative count table 320 is represented as 16 bits. With this arrangement, the tentative count adding unit 103 is able to use an SIMD instruction to add the addend data in the addend table 310 to the tentative count data at POSITION(n) through POSITION(n+3) in the tentative count table 320.

The final count adding unit 104 updates the final count table 330 based on the tentative count table 320 when the count of the counter m exceeds a predetermined value. Namely, the final count adding unit 104 adds the tentative count data in the tentative count table 320 to the final count data in the final count table 330.

The data size of the tentative count data in the tentative count table 320 of the present embodiment is 16 bits. With this arrangement, the tentative count data in the tentative count table 320 suffices to count the occurrences of mutation patterns within a range of 0 to 65535 (i.e., the range that can be expressed by use of 16 bits). The data collecting apparatus 10 of the present embodiment thus adds the tentative count data in the tentative count table 320 to the final count data in the final count table 330 when the count of the counter m becomes greater than or equal to 65536. A value of 65535 is an example of the largest value that can be expressed by the data size of the count data.

Figure 7:
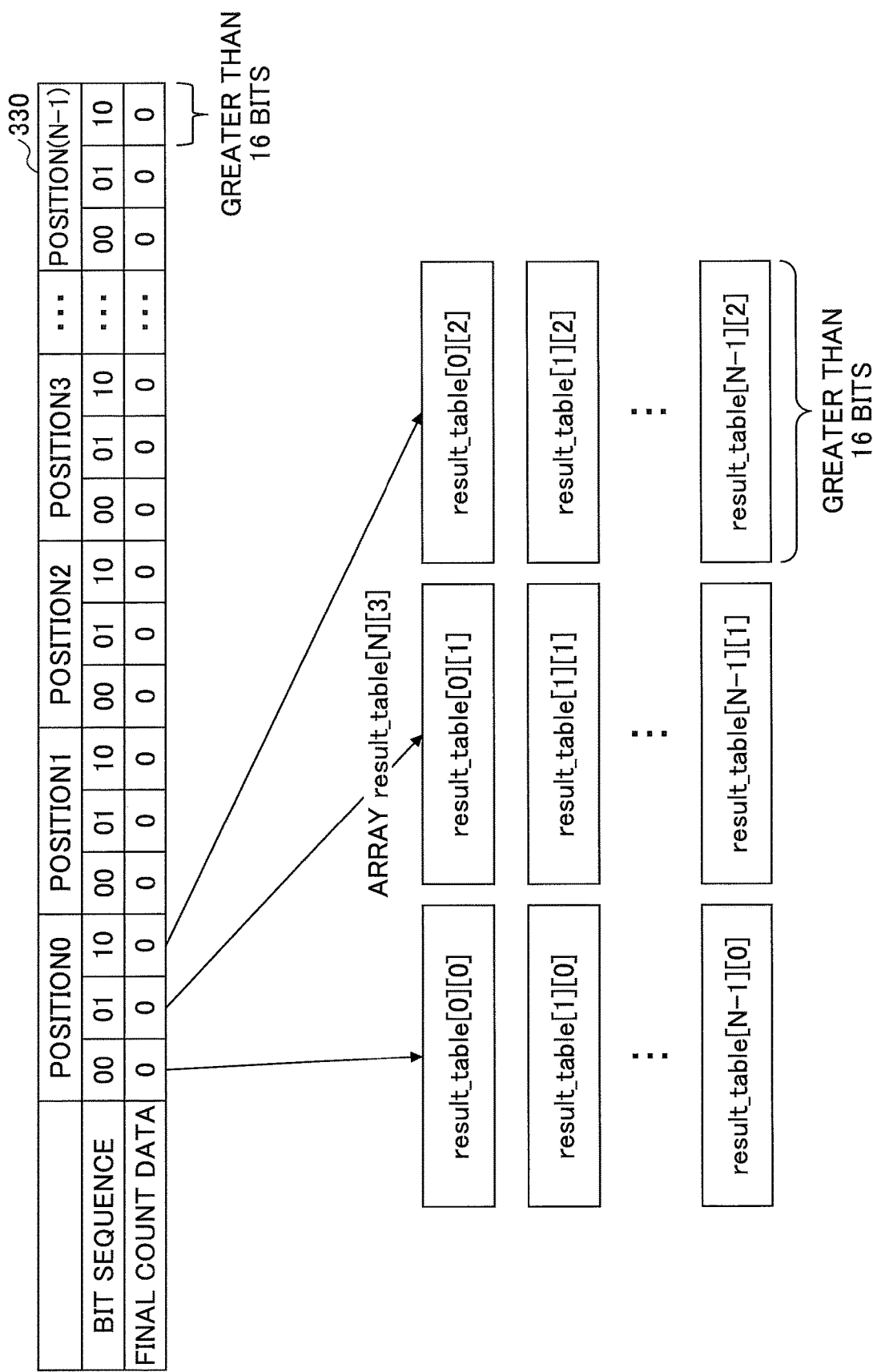
FIG. 7 is a drawing illustrating an example of a final count table.

The final count table 330 stored in the table storage unit 300 will be described by referring to FIG. 7. FIG. 7 is a drawing illustrating an example of the final count table 330.

As illustrated in FIG. 7, the final count table 330 of the present embodiment stores final count data indicative of the final counts of occurrences of mutation patterns such that the final count data are associated with positions in the genome data 400 and with bit sequences representing mutation patterns.

In the final count table 330 of the present embodiment, each final count data is represented by a larger data size (e.g., 24 bits, 32 bits, or the like) than 16 bits. Namely, the data size of final count data is larger than the data size of tentative count data (which is 16 bits).

The final count table 330 of the present embodiment may thus be implemented as result_table[N][3] which is a two-dimensional array of elements each having a larger data size than 16 bits.

The array elements "result_table[0][0]" through "result_table[0][2]" store the final count data for the bit sequences "00" through "10" at POSITION0. The array elements "result_table[1][0]" through "result_table[1][2]" store the final count data for the bit sequences "00" through "10" at POSITION1. Similarly, the array elements "result_table[N−1][0]" through "result_table[N−1][2]" store the final count data for the bit sequences "00" through "10" at POSITION (N−1).

In the manner described above, the final count table 330 stores final count data indicative of the numbers of occurrences of mutation patterns at each position in the genome data 400.

The final count table 330 has no final count data for the bit sequence "11". This is because the SNP patterns are fully represented as the bit sequences "00", "01", and "10". Alternatively, the SNP patterns may be represented as "A/A", "A/C", "C/A", and "C/C" by discriminating between the paternal line and the maternal line. In such a case, the SNP patterns are represented as the bits sequences "00", "01", "10", and "11". When this is the case, the final count table 330 may store final count data for the bit sequence "11".

Figure 8:
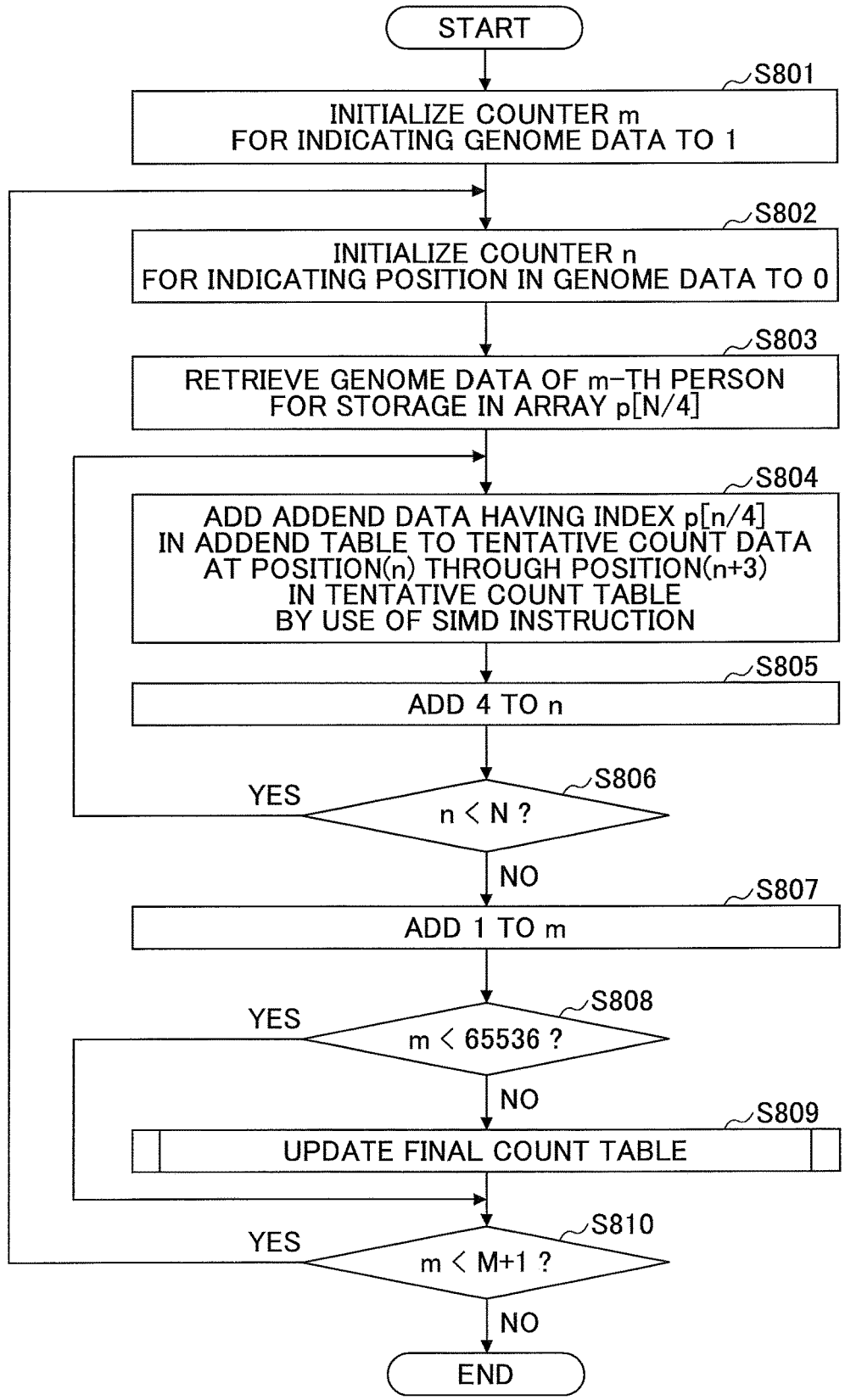
FIG. 8 is a flowchart illustrating an example of a data collection process according to the embodiment.

In the following, the data collection process performed by the data collecting apparatus 10 according to the present embodiment will be described by referring to FIG. 8. FIG. 8 is a flowchart illustrating an example of the data collection process according to the present embodiment.

At step S801, the counter controlling unit 101 sets an initial value of "1" to the counter m that indicates an m-th genome data 400-m stored in the data storage unit 200.

At step S802, the counter controlling unit 101 sets an initial value of "0" to the counter n that indicates POSITION (n) in the genome data 400.

At step S803, the data retrieving unit 102 retrieves the genome data 400-m among the genome data 400 stored in the data storage unit 200, and stores the retrieved data in p[N/4] which is an array of elements each having 8 bits.

Namely, the data retrieving unit 102 retrieves the genome data 400-m from the data storage unit 200, and stores in the array element "p[0]" the bit sequence of POSITION0 through POSITION3 in the retrieved genome data 400-m. The data retrieving unit 102 further stores in the array element "p[1]" the bit sequence of POSITION4 through POSITION7 in the genome data 400-m. Similarly, the data retrieving unit 102 further stores in the array element "p[(N/4)−1]" the bit sequence of POSITION(N−4) through POSITION(N−1) in the genome data 400-*m*.

As a result, the array element "p[i/4]" (i=0, 4, 8, . . . , N−4) has stored therein the bit sequence of POSITION(i) through POSITION(i+3) in the genome data 400-*m*.

Subsequently, the tentative count adding unit 103 extracts the bit sequence stored in the array element "p[n/4]". At step S804, the tentative count adding unit 103 refers to the addend table 310 to identify the addend data having the same index as the extracted bit sequence, and uses an SIMD instruction to add the identified addend data to the tentative count data of POSITION(n) through POSITION(n+3) in the tentative count table 320.

Namely, the tentative count adding unit 103 adds the addend data stored in the array element "sum table[p[n/4]] to the array element "tmp_table[n/4]" by use of an SIMD instruction.

In this manner, the tentative count adding unit 103 adds the addend data at the same index as the bit sequence of POSITION(n) through POSITION(n+3) in the genome data 400-*m* to the tentative count data at POSITION(n) through POSITION(n+3) in the tentative count table 320. It should be further noted that the tentative count adding unit 103 is able to add the addend data corresponding to the bit sequence for 4 positions in the genome data 400-*m* to the tentative count data for 4 positions.

At step S805, the counter controlling unit 101 adds "4" to the counter n. Namely, the counter controlling unit 101 sets n equal to n+4.

At step S806, the counter controlling unit 101 checks whether the count of the counter n is smaller than N.

When the counter controlling unit 101 determines at step S806 that the count of the counter n is smaller than N, the data collecting unit 100 returns to step S804 to perform the process thereof. Namely, the tentative count adding unit 103 performs the process of step S804 with respect to each value of n, i.e., 0, 4, 8, . . . , and N−4.

When it is determined at step S806 that the count of the counter n is not smaller than N, the counter controlling unit 101 adds "1" to the counter m (step S807). Namely, the counter controlling unit 101 sets m equal to m+1.

At step S808, the counter controlling unit 101 checks whether the count of the counter m is smaller than 65536.

This check at step S808 as to whether the count of the counter m is smaller than 65536 is made in order to ensure that no data loss occurs in the tentative count data. In consideration of this, the counter controlling unit 101 may alternatively check whether at least one of the tentative count data in the tentative count table 320 has reached 65535.

When the counter controlling unit 101 determines at step S808 that the count of the counter m is not smaller than 65536, the data collecting unit 100 uses the final count adding unit 104 at step S809 to update the final count table 330 based on the tentative count table 320. The detail of the process at this step for updating the final count table will be described later.

When the counter controlling unit 101 determines at step S808 that the count of the counter m is smaller than 65536, or immediately after step S809, the counter controlling unit 101 checks at step S810 whether the count of the counter m is smaller than M+1.

When the counter controlling unit 101 determines at step S810 that the count of the counter m is smaller than M+1, the data collecting unit 100 returns to step S802 to perform the process thereof. Namely, the data collecting unit 100 performs the processes of steps S802 through S809 with respect to each value of m, i.e., 1, 2, . . . , and M.

When the counter controlling unit 101 determines at step S810 that the count of the counter m is not smaller than M+1, the data collecting unit 100 brings the data collection process to an end. In this manner, the data collecting unit 100 counts the numbers of occurrences of mutation patterns at each position in the genome data 400.

Figure 9:
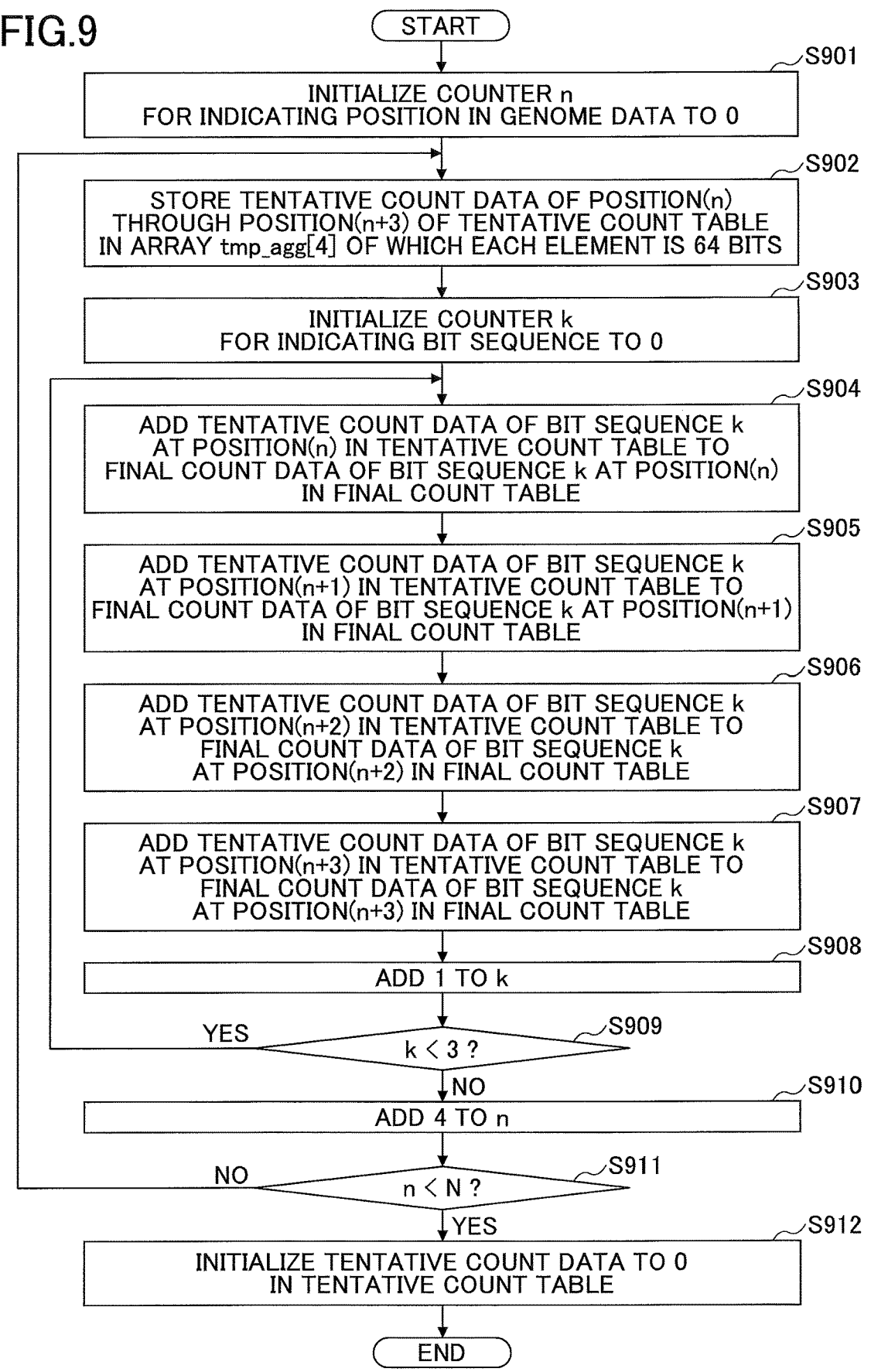
FIG. 9 is a flowchart illustrating an example of the process of updating a final count table according to the embodiment.

In the following, the process of step S809 in the data collection process (i.e., the process of updating a final count table) will be described in detail by referring to FIG. 9. FIG. 9 is a flowchart illustrating an example of the process of updating a final count table according to the present embodiment.

At step S901, the counter controlling unit 101 sets an initial value of "0" to the counter n that indicates POSITION(n) in the genome data 400.

At step S902, the final count adding unit 104 stores, in tmp_agg[4] which is an array of elements each having 64 bits, the tentative count data of POSITION(n) through POSITION(n+3) in the tentative count table 320.

Namely, the final count adding unit 104 stores in the array element "tmp_agg[0]" the tentative count data of POSITION(n) in the tentative count table 320. The final count adding unit 104 further stores in the array element "tmp_agg[1]" the tentative count data of POSITION(n+1) in the tentative count table 320. Similarly, the final count adding unit 104 further stores in the array elements "tmp_agg[2]" and "tmp_agg[3]" the tentative count data of POSITION(n+2) and POSITION(n+3) in the tentative count table 320, respectively.

At step S903, the counter controlling unit 101 sets an initial value of "0" to a counter k indicating a bit sequence. The counter k, which has 2 bits, indicates a bit sequence representing a mutation pattern. In the following, the bit sequence indicated by the counter k is denoted as the bit sequence k.

At step S904, the final count adding unit 104 adds the tentative count data of the bit sequence k at POSITION(n) in the tentative count table 320 to the final count data of the bit sequence k at POSITION(n) in the final count table 330.

Namely, the final count adding unit 104 performs a 16 k-bit right shift with respect to the array element "tmp_agg[0]", and masks the resultant data with "0x00000000000000ff", followed by adding the masked data to the array element "result_table[n][k]".

At step S905, the final count adding unit 104 adds the tentative count data of the bit sequence k at POSITION(n+1) in the tentative count table 320 to the final count data of the bit sequence k at POSITION(n+1) in the final count table 330.

Namely, the final count adding unit 104 performs a 16 k-bit right shift with respect to the array element "tmp_agg[1]", and masks the resultant data with "0x00000000000000ff", followed by adding the masked data to the array element "result_table[n+1][k]".

At step S906, the final count adding unit 104 adds the tentative count data of the bit sequence k at POSITION(n+2) in the tentative count table 320 to the final count data of the bit sequence k at POSITION(n+2) in the final count table 330.

Namely, the final count adding unit 104 performs a 16 k-bit right shift with respect to the array element "tmp_agg[2]", and masks the resultant data with "0x00000000000000ff", followed by adding the masked data to the array element "result_table[n+2][k]".

At step S907, the final count adding unit 104 adds the tentative count data of the bit sequence k at POSITION(n+3) in the tentative count table 320 to the final count data of the bit sequence k at POSITION(n+3) in the final count table 330.

Namely, the final count adding unit 104 performs a 16 k-bit right shift with respect to the array element "tmp_agg [3]", and masks the resultant data with "0x00000000000000ff", followed by adding the masked data to the array element "result_table[n+3][k]".

At step S908, the counter controlling unit 101 adds "1" to the counter k. Namely, the counter controlling unit 101 sets k equal to k+1.

At step S909, the counter controlling unit 101 checks whether the count of the counter k is smaller than 3.

The SNP patterns may be represented as "A/A", "A/C", "C/A", and "C/C", for example, by discriminating between the paternal line and the maternal line. In such a case, addition is performed with respect to the final count data of the bit sequence k at POSITION(n+4) before step S908 is performed. In this case, further, the counter controlling unit 101 checks at above-noted step S909 whether the count of the counter k is smaller than 4.

When the counter controlling unit 101 determines at step S909 that the count of the counter k is smaller than 3, the data collecting unit 100 returns to step S904 to perform the process thereof. Namely, the data collecting unit 100 performs the processes of steps S904 through S909 with respect to each value of k, i.e., 0, 1, and 2.

When the counter controlling unit 101 determines that the count of the counter k is not smaller than 3, the counter controlling unit 101 adds "4" to the counter n at step S910. Namely, the counter controlling unit 101 sets n equal to n+4.

At step S911, the counter controlling unit 101 checks whether the count of the counter n is smaller than N.

When the counter controlling unit 101 determines at step S911 that the count of the counter n is smaller than N, the data collecting unit 100 returns to step S902 to perform the process thereof. Namely, the data collecting unit 100 performs the processes of steps S902 through S910 with respect to each value of n, i.e., 0, 4, 8, . . . , and N−4.

When the counter controlling unit 101 determines at step S911 that the count of the counter n is not smaller than N, the final count adding unit 104 initializes the tentative count data to "0" in the tentative count table 320 at step S912. Namely, the final count adding unit 104 sets an initial value of "0" to the array elements "tmp_table[0]" through "tmp_table[(N/4)−1]".

In this manner, the data collecting apparatus 10 of the present embodiment counts the numbers of occurrences of mutation patterns at each position with respect to a plurality of genome data 400. In so doing, the data collecting apparatus 10 of the present embodiment identifies addend data by use of an 8-bit sequence corresponding to 4 positions in the genome data 400, and utilizes an SIMD instruction to add the identified addend data to the tentative count table 320.

With this arrangement, the data collecting apparatus 10 of the present embodiment does not need to use either a shift operation or a masking operation when counting in the tentative count table 320 the numbers of occurrences of mutation patterns at each position in the genome data 400. The data collecting apparatus 10 of the present embodiment thus enables high-speed counting of occurrences of mutation patterns at each position in the genome data 400.

The data collecting apparatus 10 of the present embodiment has been described as having the CPU 17 that is capable of processing 256-bit data in response to an SIMD instruction. This is not a limiting example, and the CPU 17 may alternatively be capable of processing 512-bit data in response to an SIMD instruction. In such a case, the data collecting apparatus 10 of the present embodiment may identify 512-bit addend data by use of a 16-bit sequence corresponding to 8 positions in the genome data 400, and may utilize an SIMD instruction to add the identified addend data to the tentative count table 320.

In this manner, the data collecting apparatus 10 of the present embodiment may use an appropriate number of bits for a bit sequence extracted from the genome data 400 and for indexes and addend data in the addend table 310 as such an appropriate number is determined in response to the number of bits of an SIMD instruction processable by the CPU 17.

Figure 10:
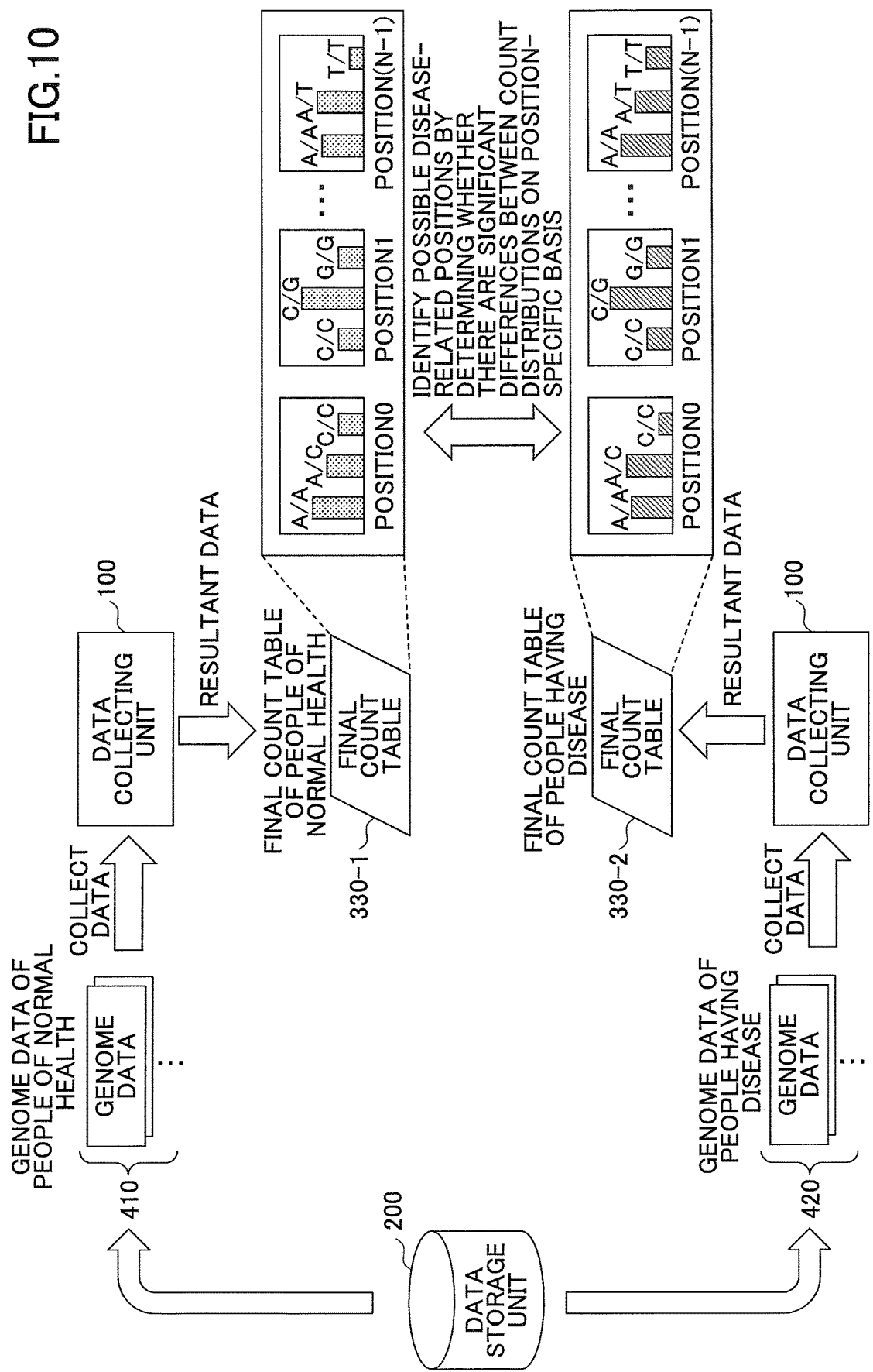
FIG. 10 is a drawing illustrating an example of identifying possible disease-related positions by use of the data collection process according to the embodiment.

In the following, identifying possible disease-related positions will be described by referring to FIG. 10 as an example of the application of the data collection process according to the present embodiment. FIG. 10 is a drawing illustrating an example of identifying possible disease-related positions by use of the data collection process according to the present embodiment.

In FIG. 10, the genome data 400 stored in the data storage unit 200 includes genome data 410 belonging to people of normal health free from a disease of interest and genome data 420 belonging to people having such a disease.

The data collecting apparatus 10 of the present embodiment counts the numbers of occurrences of mutation patterns at each position in the genome data 410 to generate a final count table 330-1 belonging to the people having no such disease. Similarly, the data collecting apparatus 10 of the present embodiment counts the numbers of occurrences of mutation patterns at each position in the genome data 420 to generate a final count table 330-2 belonging to the people having the disease.

Position-specific distributions of counted occurrences of mutation patterns (for the people having no such disease) are created based on the final count table 330-1. Also, position-specific distributions of counted occurrences of mutation patterns (for the people having the disease) are created based on the final count table 330-2.

With this arrangement, possible disease-related positions may be identified by determining whether there are significant differences between the distributions of people having no such disease and the distributions of people having the disease.

In this manner, the data collecting apparatus 10 of the present embodiment may be used in the data collection process for identifying possible disease-related positions among the positions at which SNP patterns occur in the DNA sequence. However, this is not a limiting example. The data collecting apparatus 10 of the present embodiment may equally be applicable to a data collection process for counting the numbers of occurrences of patterns when such patterns in data are represented as a bit sequence having a predetermined number of bits.

According to at least one embodiment, the time needed to collect genome data is shortened.

All examples and conditional language recited herein are intended for pedagogical purposes to aid the reader in understanding the invention and the concepts contributed by the inventor to furthering the art, and are to be construed as being without limitation to such specifically recited examples and conditions, nor does the organization of such examples in the specification relate to a showing of the superiority and inferiority of the invention. Although the embodiment(s) of the present inventions have been described in detail, it should be understood that the various changes, substitutions, and alterations could be made hereto without departing from the spirit and scope of the invention.

What is claimed is:

1. An information processing apparatus, comprising:
a memory; and
a processor coupled to the memory and configured to:
extract data having x times y bits, to produce extracted x-times-y-bit data, from genome data in which a mutation pattern at each gene mutation position is represented as x bits, such that the extracted data is constituted by y data pieces each having x bits at y respective mutation positions, x and y being integers greater than or equal to 1, respectively;
refer to an addend table by using the extracted x-times-y-bit data as an index, the addend table storing a plurality of addend data associated with respective indexes, thereby identifying addend data associated with an index identical to the extracted x-times-y-bit data to output identified addend data, the identified addend data having bit "1" at a position of a mutation pattern represented by the x bits for each one of the y mutation positions; and
determine count data indicating counts of occurrences of mutations patterns in the genome data by adding by a SIMD (single instruction multiple data) instruction the identified addend data to the count data so that the bit "1" at the position of the mutation pattern represented by the x bits is added by the SIMD instruction to the count data each of the y mutation positions in the genome data.

2. The information processing apparatus as claimed in claim 1, wherein the count data is added to final count data upon the addend data being added to the count data a number of times equal to a data size of the count data, the final count data having a larger data size than the count data.

3. The information processing apparatus as claimed in claim 1, wherein the addend data and the count data have a data size equal to 16 bits.

4. A non-transitory recording medium having a program stored therein for causing a computer to perform:
extracting data having x times y bits, to produce extracted x-times-y-bit data, from genome data in which a mutation pattern at each gene mutation position is represented as x bits, such that the extracted data is constituted by y data pieces each having x bits at y respective mutation positions, x and y being integers greater than or equal to 1, respectively; and
referring to an addend table by using the extracted x-times-y-bit data as an index, the addend table storing a plurality of addend data associated with respective indexes, thereby identifying addend data associated with an index identical to the extracted x-times-y-bit data to output identified addend data, the identified addend data having bit "1" at a position of a mutation pattern represented by the x bits for each one of the y mutation positions, and determining count data indicating counts of occurrences of mutation patterns in the genome data by adding by a SIMD (single instruction multiple data) instruction the identified addend data to the count data so that the bit "1" at the position of the mutation pattern represented by the x bits is added by the SIMD instruction to the count data in each of the y mutation positions in the genome data.

5. A method of collecting genome data, comprising as processes performed by a computer:
extracting data having x times y bits, to produce extracted x-times-y-bit data, from genome data in which a mutation pattern at each gene mutation position is represented as x bits, such that the extracted data is constituted by y data pieces each having x bits at y respective mutation positions, x and y being integers greater than or equal to 1, respectively; and
referring to an addend table by using the extracted x-times-y-bit data as an index, the addend table storing a plurality of addend data associated with respective indexes, thereby identifying addend data associated with an index identical to the extracted x-times-y-bit data to output identified addend data, the identified addend data having bit "1" at a position of a mutation pattern represented by the x bits for each one of the y mutation positions, and determining count data indicating counts of occurrences of mutation patterns in the genome data by adding by a SIMD (single instruction multiple data) instruction the identified addend data to the count data so that the bit "1" at the position of the mutation pattern represented by the x bits is added by the SIMD instruction to the count data in each of the y mutation positions in the genome data.

* * * * *